United States Patent [19]

Judge et al.

[11] 4,047,032
[45] Sept. 6, 1977

[54] STANDARD FOR SPECTRAL REFLECTANCE

[75] Inventors: John F. X. Judge; Jerome Salpeter, both of Yorktown Heights, N.Y.

[73] Assignee: Technicon Instruments Corporation, Tarrytown, N.Y.

[21] Appl. No.: 585,008

[22] Filed: June 9, 1975

[51] Int. Cl.$^2$ .................... G01N 21/22; G01N 21/48
[52] U.S. Cl. .................... 250/338; 250/252; 356/51; 356/210; 356/243
[58] Field of Search .............. 250/252, 228, 338–341; 356/51, 191, 192, 194, 209–212, 236, 243

[56] References Cited

U.S. PATENT DOCUMENTS

| 3,504,963 | 4/1970 | Davies et al. | 250/228 X |
| 3,776,642 | 12/1973 | Anson et al. | 356/188 |

OTHER PUBLICATIONS

Price List of the Diano/Hardy Spectrophotometer, Pl. 101, July 15, 1970, pp. 1 and 2.

Primary Examiner—F. L. Evans
Attorney, Agent, or Firm—S. P. Tedesco; Stephen E. Rockwell

[57] ABSTRACT

A standard, which is of ceramic material and preferably includes alumina, for spectral reflectance for use in near infrared reflectance measurements of constituents of samples, which constituents comprise oil, moisture and protein. The standard reflects electromagnetic radiation in the wavelength range of 1.0 – 2.5 micrometers and exhibits its best optical characteristics in the operational range of 1.4 – 2.4 micrometers.

2 Claims, 1 Drawing Figure

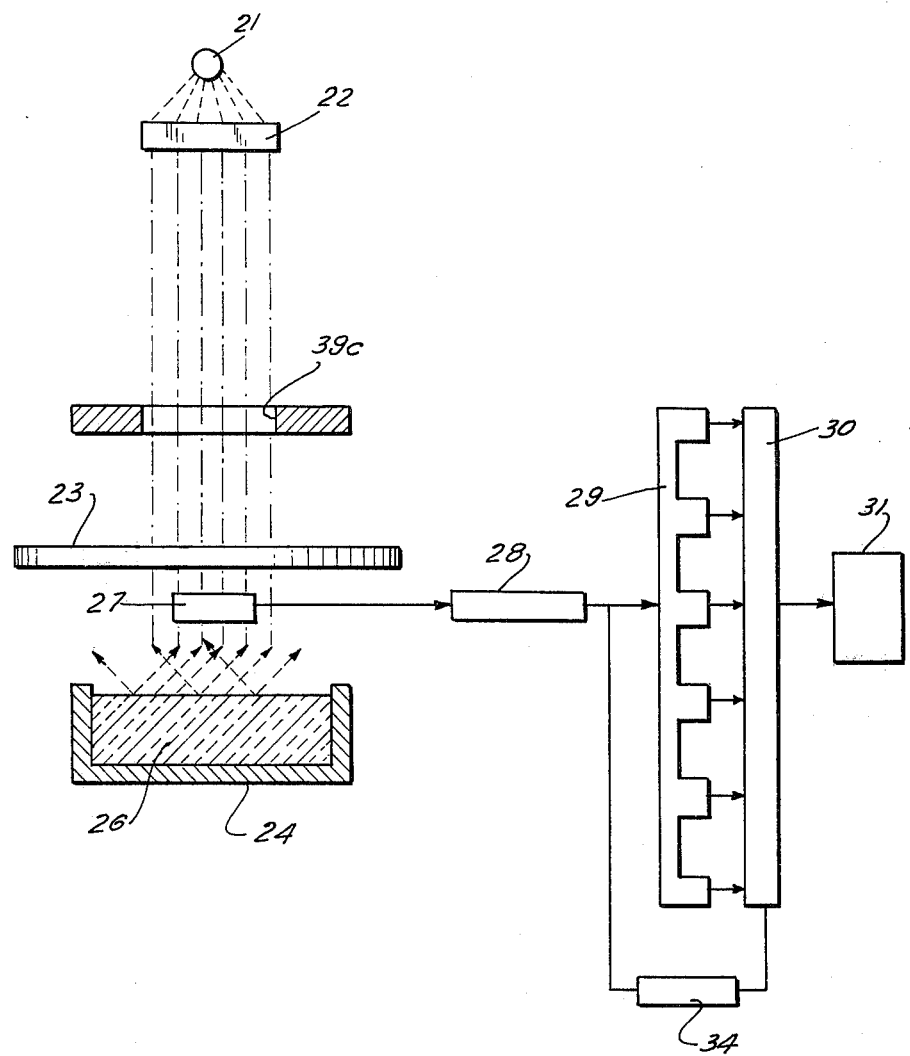

STANDARD FOR SPECTRAL REFLECTANCE

BACKGROUND OF THE INVENTION

1. Field of the Invention

This invention relates to a standard for spectral reflectance for use in calibrating an automated infrared reflectance analyzer for quantitation of constituents of interest of samples.

2. Prior Art

Prior known standards for spectral reflectance for use in infrared reflectance measurements of the general type performed by the analyzer described in Anson et al. U.S. Pat. No. 3,776,642 have been structured of Teflon polytetraflouroethylene resin of either powdered or solid form, powdered barium sulfate, powdered magnesium oxide and a nickel alloy having a porous reflective surface. Such powders, which are used in unbound and uncoated form, exposed to the ambient atmosphere in use, have adsorbed thereon from the latter substances such as dust, oils, tars and oxides of nitrogen and sulfur and other chemical substances, for example, which adversely affect the usefulness of such powdered substances as standards by a change in the ratio of the incident light to the reflectivity of such light from such substances. Obviously, such standards in powdered form cannot be cleaned readily of such foreign substances. A coated surface of magnesium oxide has been used as such a reflective standard. For this purpose, magnesium ribbon has been burned under a support surface. The resulting vapor containing magnesium oxide then coats the support surface. Such a standard consists of magnesium oxide which is fragile and difficult to clean.

Inasmuch as such analyzers have extensive use at rail and truck terminals and grain storage facilities as well as other places, as brought out in the aforementioned Anson et al U.S. Patent, where the environment is dusty and polluted with chemicals these standards in the form of powder usually require replacement after a relatively short period of use, say one day to a week, depending on environmental conditions.

Further, such standards of exposed, powder form, like all other standards for spectral reflectance, must present a reflective surface which is smooth and uniformly flat in a plane normal to the incident radiation. The unbound, exposed powder may shift, though compacted to at least some extent, even in normal handling, particularly as movement of the standard from registry with the incident light to a position out of such registry is required in such analysis to permit the position of the sample to be switched with respect to the registry position of the standard. Such shifting of the powder in the standard changes the reflective characteristics of the standard and the reflective surface thereof must be re-smoothed as with a spatula.

Exposed barium sulfate and magnesium oxide in the required dehydrated form absorb moisture which adversely affects the reflectance characteristics of such powders as standards by changes in the ratio of incident light to reflected light. These powders require frequent drying out in an oven which is costly and inconvenient. Humidity is also known to adversely affect at least the use of certain ones of these powders as such standards by a change in the aforementioned ratio, and the reflective surface area presented by all of the aforementioned powders lacks the desired degree of homogeneity.

An attempt to hermetically seal such standards to protect them from moisture and foreign substances, such as by enclosure in glass which by interfacing with the powder tends at least to some extent to maintain a degree of material flatness and smoothness of the powder, has been found to interfere with the desirable diffuse reflectance of the powder and results in a more specular and less diffuse reflectance caused by the glass cover. Further, such glass-powder interface may develop interference fringes altering the reflective characteristic of the standard.

In the use in the prior art of solid or powdered Teflon resin as an infrared standard of reflectance in accordance with the aforementioned Anson et al Patent, the material was found to be relatively transmissive of light and when used as a reflective standard, incident light on a surface thereof has shown a marked tendency to be reflected or absorbed by a support for such standard in opposing relation to the surface of the standard opposite the first mentioned surface thereof. This is a disadvantage in its use as such a standard, particularly noticeable in the usual approximately 3/8 in. thickness of solid Teflon material supplied for such use and even more noticeable in lesser thicknesses. In addition, for such uses as a standard in such analyses, the solid Teflon material must be machined to provide the requisite degree of material flatness and smoothness of the reflective surface in a plane normal to the incident light. Such surface must be perfectly smooth and without scratches or other nonuniformities. The softness of such Teflon material renders it easily marred and therefore damaged as to its reflective characteristics as by wiping with a cloth and even more by scrubbing to remove deposits of dust and chemicals deposited thereon in use as previously described. For this reason attempts have been made to clean the reflective surface of such material by spraying substances thereon such a Freon fluorochlorohydrocarbon but such cleansing results in residues of cleaning substances being left on such reflective surface which adversely affect the ratio of incident light to light reflected from the surface by a change in such ratio. Neotec Corporation of Rockville, Md., supplies a standard for reflectance known as a "white tile." It is a relatively thin square comprising solid Teflon polytetraflouroehylene and not, as its name suggests, a ceramic material.

A standard for spectral reflectance for use in the analyzer of the Anson et al U.S. Pat. No. 3,776,641 should exhibit light reflectance equally throughout the operational wavelength range of the analyzer. Additionally, the light absorption of the standard should be unvarying throughout this wavelength range. These properties are hereinafter referred to as "optical flatness." If the percentage of incident light absorbed by the standard at a particular wavelength in the operational range is higher, there is a resultant decrease in the percentage of light reflected and a deviation from optical flatness. All the aforementioned prior art standards for spectral reflectance in varying degrees do not exhibit this optical flatness, without consideration of such factors as service life described above. Of various prior art standards tested at the instigation of the assignee of the present invention, a porous nickel alloy surface came closest to such optical flatness in the last-mentioned operational range and, more precisely and restrictively, in the range of 1.4 –2.4 micrometers. However such nickel alloy standard is subject to the drawbacks that, at best, it is extremely difficlt to duplicate in fabrication in a manner to obtain the same reflectance characteristics, similar to other prior art reflectance standards discussed hereinbefore. It clogs with dust and cannot be cleaned easily and quickly.

Teflon polytetrafluoroethylene resin, in either powder or solid form, exhibits reflection peaks in the region of 2.15 micrometers which is the wavelength region most important in the determination of protein in samples. Substantial change in the characteristics of spectral reflectance of the material of such standard in this region was noted as being attributable to such reflection peaks. Other aforementioned materials of the aforementioned prior art standards have varying light reflection characteristics over such operational wavelength range from lot to lot because of the difficulty of uniform manufacture.

The present invention overcomes these difficulties with such prior art reflectance standards.

SUMMARY OF THE INVENTION

One object of the invention is to provide an improved standard of spectral reflectance for near infrared reflectance measurements. Another object is to provide such a standard which reflects electromagnetic radiation in the wavelength range between 1.0 and 2.5 micrometers and exhibits its best optical characteristics as a standard between the operational range of 1.4 and 2.4 micrometers, the effective reflective radiation being of a diffuse rather than a specular nature.

Still another object is to provide such a standard to retain the above-mentioned reflective properties after repeated, routine cleansing procedures consisting of soft-fiber brushing, cloth wiping, organic solvent washing, soap and detergent washing, and rinsing. Further, there is provided a reflective standard having a reflective surface which is opaque. non-porous, non-permeable to moisture, resistant to chemicals in which is comes in contact in use, and has a high density. Such a standard may be formed of a fired ceramic of the type having these properties and the added, significant property of being resistant to all types of abrasives except those approaching the hardness of diamonds. Such a ceramic material may be formed of a suitable aluminum oxide having, together wit these properties, a high degree of purity, which has a reflective surface for irradiation by incident light which surface is smooth and planar "as fired".

BRIEF DESCRIPTION OF THE DRAWING

The drawing is a simplified schematic diagram illustrating the basic principles of operation of apparatus utilizing the improved reflectance standard of this invention.

DETAILED DESCRIPTION OF THE PREFERRED EMBODIMENTS

In accordance with the invention, there is provided a standard for spectral reflectance for use in near infrared reflectance measurements of constituents by weight such as oil, moisture and protein, for example, in samples such as grain, oil seeds, dry milk products, meat products and blends therefor, for example. It has usefulness in the infrared reflectance analyzer of Anson et al U.S. Pat. No. 3,776,642 as a replacement, exhibiting optical qualities superior to those of such analyzer, for the standard of Teflon resin described in the patent. For such use, the instant standard is a solid disc. The disclosure of U.S. Pat. No. 3,776,642 is incorporated by reference.

In the drawing, a light source 21 produces infrared light rays impinging on a collimating lens 22 which causes the infrared rays to be projected through an aperture mask 38 c and a filter wheel 23 in substantially a parallel configuration as indicated by the broken lines. When a discrete filter element of rotatable filter wheel 23 is in registry with the light source 21 and a receptacle 24 positioned therebeneath, a quantity of infrared radiation impinges the surface of a reflectance standard 26 positioned within receptacle 24 so that only reflected rays, indicated by the angularly disposed arrowed lines, are directed upwardly from the surface of the standard to impinge upon a photocell 27, which is infrared sensitive. It is to be understood that the sample to be analyzed, not shown, would occupy the registry position of the standard 26, when the latter is out of such registry. Preferably, photocell 27 is positioned intermediate filter wheel 23 and standard receptacle 24. The top of the photocell 27 is shielded, so that only light rays reflected upwardly from standard 26 produce an output signal. The output of photocell 27 is connected to the input of an electronic amplifier 28. The output of amplifier 28 is connected to the input of a sample and hold circuit 29. Preferably, there are six channels in the sample and hold circuit 29, one channel for each of six different filter elements of the filter wheel 23 which is rotatable. The outputs of the sample and hold circuit 29 are connected to a computer logic circuit 30, which includes a resistor and diode matrix arrangement for providing summation information of the signals produced by the photocell 27. Preferably, the amplitude of such signals are converted into voltages having logarithmic characteristics, which are added in the resistor matrix. The output of the computer logic circiut 30 is deleivered to a digital readout 31. To insure that the pulses are inserted into the proper corresponding channels of saple and hold circuit 29, a synchronizing circuit means 34 is connected mechanically, by non-illustrated means, with the filter wheel 23 and electrically connected with the computer logic circuit 30 and the output of the amplifier circuit 28.

The standard 26 of the invention reflects for detection electromagnetic radiation in the wavelength range of 1.0 – 2.4 micrometers and essentially exhibits light reflectance equally throughout the operational range of 1.4 – 2.4 micrometers. Additionally, the light absorption of the standard 26 is essentially unvarying throughout this wavelength range. As previously indicated, these properties in combination are referred to herein as "optical flatness." Further, the standard 26, has relatively low light transmissive characteristics, nonporosity, high density, homogeneity, nonpermeability to moisture, and high resistance or inertness to chemicals in the environment of its use, e.g., oxides of nitrogen and sulfur. Such a standard 26 may be formed of a ceramic material of the type having these properties, and the added and very significant property of being highly resistant to all types of abrasives except diamond abrasives. Such a ceramic material may be formed, for example, of a suitable aluminum oxide having, together with these properties, a high degree of purity. It has a reflective surface, for irradiation by incident light in a plane normal thereto, which surface is smooth and planar. However, it should be noted that the purity of the aluminum oxide is not in itself a criterion. For example, some commercially available aluminum oxides having a relatively very high degree of purity, for example, are not suitable for use. The ceramic material may be cast and suitable for the purpose "as fired". If desired, the reflective surface may be machined by grinding and/or lapping, but this does not at present appear to enhance the properties of the reflective surface of the standard 26. The planar hemogenous reflective surface of the standard is of sufficient dimensional area that the standard is independent within reasonable limits to displacement in a direction perpendicular to the direction of collimated incident light.

It is believed that heretofore all standards for near infrared reflectance having a dull reflective surface as opposed to a shiny or bright surface have been pure white to the eye, and that this is equally true of standards for reflectance used in the visible light wavelengths range. Contrary to expectations, it was discovered that a material of which the standard 26 of the invention is preferably presently structured is off-white. It may have a pink or brown tinge. It is theorized that such off-white materials were avoided in the past in the belief that any color differences would lead to different light absorption characteristics of the material and, hence, differences in light reflectance characteristics. However, visible reflectance characteristics (color) are not necessarily relevant for a near infrared standard.

EXAMPLE

A standard for near infrared spectral reflectance was cast in the form of a disc having the dimensions of 2 × 3/32 inches of a recrystalized alumina ceramic having the following formulation by weight:

| | | |
|---|---|---|
| $Al_2O_3$ | 99.82% | Approx. |
| $SiO_2$ | .08% | Approx. |
| $M_gO$ | .07% | Approx. |
| $CaO$ | .01% | Approx. |
| $Fe_2O_3$ | .035% | Approx. |
| $Na_2O$ | <.001% | Approx. |
| $K_2O$ | <.005% | Approx. |

The disc was smooth and planar as fired and when tested in this condition, for any varying of the ratio of the intensity of irradiated collimated light in a pland normal to either one of such planar surfaces to the intensity of the diffuse reflected light throughout finite wavelength band widths in the wavelength range of 1.4 – 2.4 micrometers from one such planar surface in the temperature range of 50° – 100° F, was found to be essentially unvarying and optically flat. More specifically, when the subject ceramic disc was tested it was found that, within the temperature range of 5° to 49° C (when compared to itself at room temperature) it had diffuse characteristics of reflectance and otical flatness which did not change within a wavelength range of 1.4 – 2.4 micrometers by more than ± 3% absolute. When the subject ceramic disc was tested for light transmission characteristics (a more definitive measurement of optical flatness) in the wavelength range of 1.4 – 2.4 micrometers, it was found to be essentially optically flat with no anomalous peaks. Ceramic material was found to have a typical hardness of 79 Rockwell 45N, a typical specific gravity of 3.82, no measurable water absorption characteristic and a coefficient of linear thermal expansion of 6.7 × $10^{-6}$ per degree centigrade in the range of 25° – 200° C.

For purposes of comparison, a prior art standard of spectral reflectance structured of Teflon solid polytetraflouroethylene resin complying with U.S. Aerospace Material Specifications AMS 3651C was cut in disc form from molded or extruded rod stock and machined to size 1¾ × ⅜ inch and ground to provide a smooth and planar reflective surface. When the Teflon disc was tested in this condition for any varying of the ratio of the intensity of irradiated collimated light in a plane normal to said planar surface to the intensity of the diffuse reflected light throughout finite wavelength band widths in the range of 1.4 – 2.3 micrometers in the temperature range of 50° – 100° F it was found to be significantly less optically flat than the ceramic standard. More specifically, when the Teflon standard was tested it was found that it had a pronounced peak centered at approximately 2.15 micrometers and extending between approximately 1.98 – 2.22 micrometers. The peak adversely affects theuse of this standard for reflectance measurements of proteinaceous samples.

The hardness of the ceramic standard 26, together with its high density and nonpermeability to moisture, render it (either planar surface thereof as cast may be used for reflectance of near infrared radiation) immune to damage from routine, periodic cleansing to remove accumulations of dust and other foreign substances, e.g., oils and tars adsorbed from the atmosphere. Such cleansing may consist of any of the following: brushing, wiping with a cloth, use of organic solvents, washing with soap or detergents and rinsing. Such foreign substances, if allowed to accumulate interfere with the ratio between incident radiation of and diffuse reflective radiation from the planar surface of the standard 26. Such characteristics of the standard make for a relatively very long service life as opposed to standard of barium sulfate, magnesium oxide and solid or powdered Teflon polytetraflouroethylene resins. Another significant advantage of the standard of spectral reflectance of the invention is the ease and simplicity with which it may be reproduces or fabricated essentially without change in its reflectance characteristics. There is also provided for use in near infrared reflective measurements of constituents of samples, an analyzer which such a standard.

While several forms of the invention have been described herein, it will be apparent, especially to those versed in the art, that the invention may take other forms and is susceptible to various changes in details without departing from the principles of the invention.

What is claimed is :

1. In an analyzer for quantitation of at least one constituent of interest of a sample by near infrared reflectance measurements, having means for irradiating a sample and a calibrating standard with light in the near infrared spectral region, detector means for receiving diffuse reflected light from said sample and said standard, said standard having known reflectance characteristics in said spectral region, and means displaying the analytical results, the improvement wherein: said standard comprises a fired ceramic element having a surface for irradiation by said irradiating means to diffusely reflect said light, said element further having a thickness to be selfsupporting and having diffusivity and relatively low transmissive characteristics such that the characteristics of said reflected light are substantially determined by the material composing said element and are essentially optically flat in the wavelength range of 1.4-2.4 micrometers.

2. In an analyzer for quantitation of at least one constituent of interest of a sample by near infrared reflectance measurements, having means for irradiating a sample and a calibrating standard with light in the near infrared spectral region, detector means for receiving diffuse reflected light from said sample and said standard, such standard having known reflectance characterisitics in said spectral region, and means displaying the analytical results, the improvement wherein: said standard comprises a fired ceramic element having a surface for irradiation by said irradiating means to diffusely reflect said light, said element further having thickness to be self-supporting and having diffusivity and relatively low transmissive characteristics such that the characteristics of said reflected light are substantially determined by the material comprising said element and are essentially optically flat in the wavelength range of 1.4–2.4 micrometers, and wherein said standard comprises alumina.

* * * * *